US00PP31383P2

(12) United States Plant Patent
Lee

(10) Patent No.: US PP31,383 P2
(45) Date of Patent: Jan. 21, 2020

(54) ***TERNSTROEMIA* PLANT NAMED 'BLTG01'**

(50) Latin Name: *Ternstroemia gymnanthera*
Varietal Denomination: BLTG01

(71) Applicant: Robert Lee, Independence, LA (US)

(72) Inventor: Robert Lee, Independence, LA (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 16/350,807

(22) Filed: Jan. 11, 2019

(51) Int. Cl.
*A01H 5/00* (2018.01)

(52) U.S. Cl.
USPC ..... Plt./226

(58) Field of Classification Search
USPC ..... Plt./226
CPC ..... A01H 5/00
See application file for complete search history.

*Primary Examiner* — Annette H Para
(74) *Attorney, Agent, or Firm* — Cassandra Bright

(57) ABSTRACT

A new and distinct *Ternstroemia* cultivar named 'BLTG01' is disclosed, characterized by distinctive dark green with a strong red-bronze flush when immature. Plants have a compact habit and are easily maintained in the landscape with minimal pruning. Leaves hold up well in direct sunlight with minimal leaf yellowing or scorching. The new cultivar is a *Ternstroemia*, suitable for ornamental garden purposes.

1 Drawing Sheet

Latin name of the genus and species: *Ternstroemia gymnanthera.*

Variety denomination: 'BLTG01'.

BACKGROUND OF THE INVENTION

The new *Ternstroemia* cultivar is a product of a planned breeding program conducted by the inventor in Independence, La. The objective of the breeding program was to produce new *Ternstroemia gymnanthera* varieties for landscape use. The open pollination resulting in this new variety was made during the Fall of 2008. The seed parent variety is an unnamed, unpatented *Ternstroemia gymnanthera*. The pollen parent is unidentified.

After identifying the new variety as a potentially interesting selection, the inventor first propagated 'BLTG01' by terminal vegetative cuttings during the Summer of at the same commercial nursery in Independence, La. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'BLTG01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BLTG01' These characteristics in combination distinguish 'BLTG01' as a new and distinct *Ternstroemia* cultivar:

1. More compact growth habit.
2. Glossy leaves with red-bronze coloration in new growth.
3. Leaves hold up well in direct sunlight with minimal leaf yellowing or scorching.

4. Easy to maintain desired shape with pruning.
5. Can reach six to eight feet high and four to five feet wide in the landscape in 10 years without pruning.

COMPARISON TO PARENT VARIETY

The new variety is similar to the seed parent variety in most horticultural characteristics. However, 'BLTG01' differs from the parent variety in the following:

1. Plants of the new variety are much more tolerant of full sun than plants of the parent.
2. Foliage of the new variety has more red-bronze immature foliage coloration than immature foliage of the seed parent.
3. Plants of the new variety are smaller than plants of the parent variety.

COMMERCIAL COMPARISON

'BLTG01' can be compared to the commercial variety *Ternstroemia gymnanthera* 'Contherann', U.S. Plant Pat. No. 11,737. Plants of the new cultivar 'BLTG01' are similar to plants of 'Contherann' in most horticultural characteristics, however, plants of the new cultivar 'BLTG01' differ in the following:

1. Plants of the new variety are smaller than plants of this comparator. Plants of BLTG01' reach approximately 6 to 8 feet high at maturity, plants of this comparator reach about 10 to 12 feet in height at maturity.
2. Plants of the new variety tolerate sun without scorching or yellowing better than this comparator.
3. Foliage of the new variety is narrower than foliage of this comparator.

'BLTG01' can be compared to the commercial variety *Ternstroemia gymnanthera* 'Conthery', U.S. Plant Pat. No. 11,735. Plants of the new cultivar 'BLTG01' are similar to plants of 'Conthery' in most horticultural characteristics, however, plants of the new cultivar 'BLTG01' differ in the following;

1. 1. Plants of the new variety are smaller than plants of this comparator. Plants of BLTG01' reach approximately 6 to 8 feet high at maturity, plants of this comparator reach about 8 to 10 feet in height at maturity.
2. Foliage of 'BLTG01' is smaller than foliage of 'Conthery'.
3. Foliage of 'BLTG01' is darker green at maturity than foliage of 'Conthery'.
4. Young foliage of 'BLTG01' is darker red-bronze than immature foliage of 'Conthery'.

BRIEF DESCRIPTION OF THE PHOTOGRAPH

The accompanying photograph illustrates in full color immature with a dark red-bronze flush as well as the dark green mature foliage. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BLTG01' plants grown outdoors in Loxley, Ala. Plants are approximately 2 years old, in a 3 gallon nursery container. Measurements and numerical values represent 9 averages of typical plant types.

Botanical classification: *Ternstroemia gymnanthera* 'BLTG01'.

PROPAGATION

Typically by softwood cuttings in Spring and Fall.

Root description: Very dense fibrous roots. Colored near RHS Grey-Brown 199C. Somewhat shallow rooted.

PLANT

Growth habit: Globular evergreen shrub.

Height: Approximately 70 cm.

Plant spread: Approximately 50 cm.

Branching characteristics: Moderately well branched, approximately 3 to 6 primary branches from the center of the plant. Branches occur at approximately 10° to 35° angles. Each primary branch has 2 to 4 lateral branches.

Primary branches:

Length of primary branches: Average range 15 to 25 cm, then branching into further laterals.

Diameter of primary branches: Approximately 6 to 1.2 mm.

Primary branch strength: Moderately strong and slightly flexible.

Primary branch color: Oldest wood near RHS Grey 201A. Immature branches near Brown 200D. New Growth near Yellow-Green 144A.

Primary branch texture: Glabrous. Oldest wood somewhat rough, but not scaly.

*Lenticels.*—Density: Dense. Shape: Flattened oblong. Size: About 0.5 mm long and 0.7 mm wide.

Lateral branches:

Length of lateral branches: Average range 7 to 18 cm.

Diameter of lateral branches: Average 4 mm.

Lateral branch strength: Moderately strong.

Lateral branch color: Near RHS Brown 200D.

Lateral branch texture: Rough.

Internode length: Average 2.0 to 3.5 cm.

Age of plant described: Approximately 2 years.

FOLIAGE

Leaf:

*Type.*—Simple.

*Arrangement.*—Alternate to nearly whorled in uppermost section.

*Average length.*—Approximately 4.5 to 6.5 cm.

*Average width.*—Approximately 1.5 to 1.9 cm.

*Shape of blade.*—Elliptic.

*Apex.*—Acute.

*Base.*—Attenuate.

*Attachment.*—Short petiolate.

*Margin.*—Entire.

*Texture of top surface.*—Glabrous.

*Texture of bottom surface.*—Glabrous.

*Appearance of top surface.*—Very glossy.

*Appearance of bottom surface.*—Matte.

*Color.*—Youngest foliage upper side: Newest foliage near Yellow-Green N144A, heavily flushed Greyed-Red 178A. Youngest foliage under side: Near Yellow-Green N144B. Margin Greyed-Purple 183A. Immature foliage upper side: Near 146A heavily flushed(covering entire blade thickly) Greyed-Purple 183A. Immature foliage under side: Near Yellow-Green 146B. Margin Greyed-Purple 183A. Mature foliage upper side: Near Green 139A. Mature foliage under side: Near Green 139C.

Venation:

*Type.*—Pinnate.

*Venation color upper side.*—Near Green 139C.

*Venation color under side.*—Mid-vein near Yellow-Green 144C. Lateral veins indistinguishable from leaf blade.

FLOWER

Flowering not observed to date.

OTHER CHARACTERISTICS

Disease and pest resistance: Neither resistance nor susceptibility to normal diseases and pests of *Ternstroemia* observed.

Temperature tolerance: USDA Zone 7 through 10.

Fruit/seed production: Not observed to date.

What is claimed is:

1. A new and distinct cultivar of *Ternstroemia* plant named 'BLTG01' as herein illustrated and described.

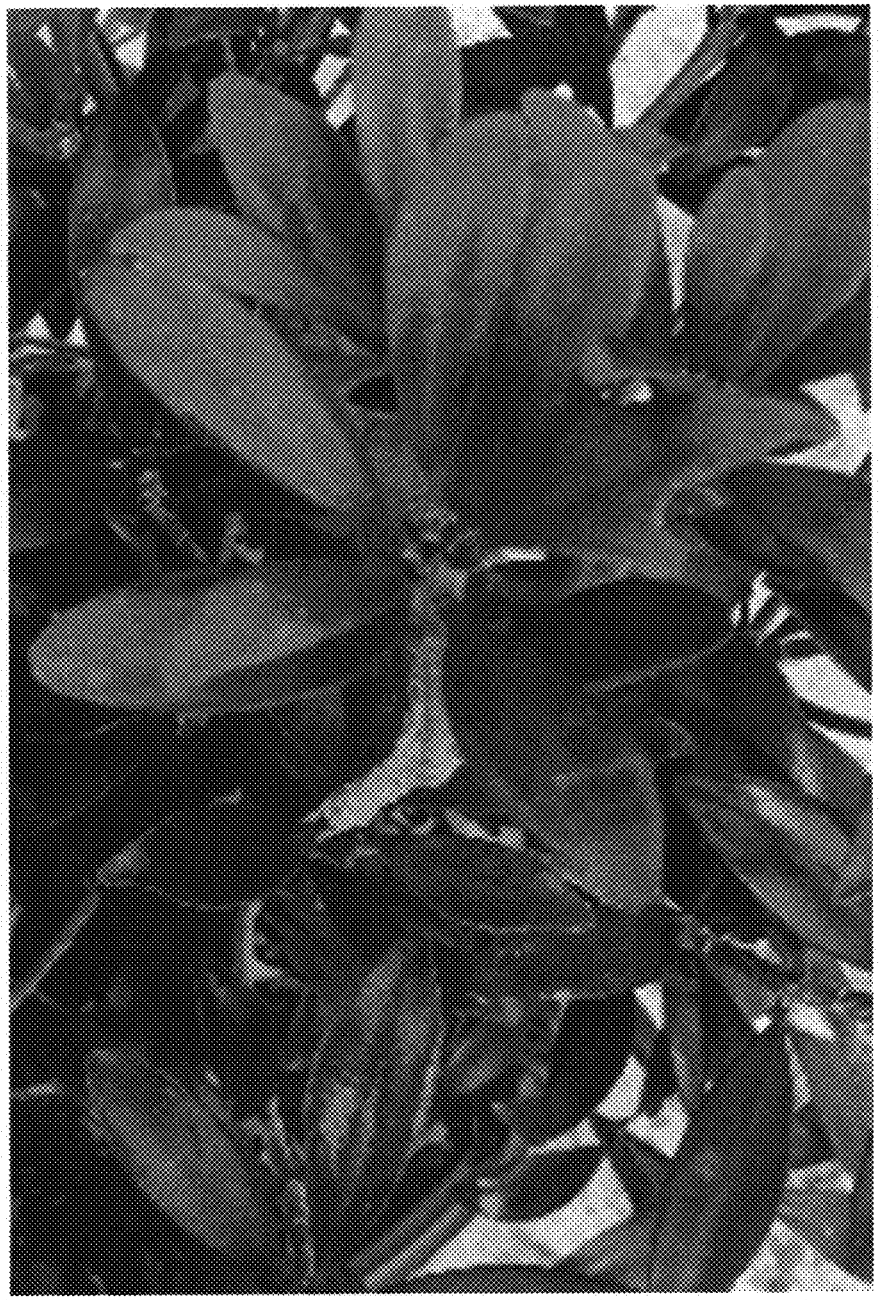

* * * * *